US011701163B2

(12) United States Patent  
Marion (10) Patent No.: US 11,701,163 B2  
(45) Date of Patent: Jul. 18, 2023

(54) ELECTROSURGICAL OUTPUT STAGE WITH INTEGRATED DC REGULATOR

(71) Applicant: Intuitive Surgical Operations, Inc., Sunnyvale, CA (US)

(72) Inventor: Duane W. Marion, Scottsdale, AZ (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 800 days.

(21) Appl. No.: 16/616,717

(22) PCT Filed: May 31, 2018

(86) PCT No.: PCT/US2018/035444  
§ 371 (c)(1),  
(2) Date: Nov. 25, 2019

(87) PCT Pub. No.: WO2018/222903  
PCT Pub. Date: Dec. 6, 2018

(65) Prior Publication Data  
US 2021/0282833 A1 Sep. 16, 2021

Related U.S. Application Data

(60) Provisional application No. 62/513,287, filed on May 31, 2017.

(51) Int. Cl.  
*A61B 18/12* (2006.01)  
*H02M 3/158* (2006.01)  
*A61B 18/00* (2006.01)

(52) U.S. Cl.  
CPC ......... *A61B 18/1206* (2013.01); *H02M 3/158* (2013.01); *A61B 2018/00767* (2013.01); *A61B 2018/1266* (2013.01)

(58) Field of Classification Search  
CPC ...... A61B 18/1206; A61B 2018/00648; A61B 2018/00767; A61B 2018/00779;  
(Continued)

(56) References Cited

U.S. PATENT DOCUMENTS

2006/0290336 A1* 12/2006 Bazes .................. H02M 3/156  
323/312  
2008/0007980 A1   1/2008 Fujiwara  
2013/0134953 A1   5/2013 Shi et al.  
(Continued)

FOREIGN PATENT DOCUMENTS

CN       1604001 A    4/2005  
CN     101355840 A    1/2009  
(Continued)

OTHER PUBLICATIONS

International Search Report and Written Opinion for Application No. PCT/US2018/035444, dated Aug. 30, 2018, 15 pages.  
(Continued)

*Primary Examiner* — Michael F Peffley  
*Assistant Examiner* — Samantha M Good  
(74) *Attorney, Agent, or Firm* — Schwegman, Lundberg & Woessner, P.A.

(57) ABSTRACT

A DC-to-DC voltage regulator circuit comprising: an output node; a pull-up switch and a pull-down switch with an output node coupled between them; a reactive circuit element coupled to the output node; a pull-up setting voltage circuit coupled to provide a pull-up setting voltage that is a function of a voltage at the output node; a pull-down setting voltage circuit coupled to provide a pull-down setting voltage that is a function of the voltage at the output node; a first comparator coupled to cause the pull-up switch to transition between open switch state and its closed switch state based upon a comparison of the pull-up setting voltage and a control voltage; and a second comparator coupled to cause  
(Continued)

the pull-down switch to transition between its open switch state and its closed switch state.

24 Claims, 6 Drawing Sheets

(58) Field of Classification Search
CPC .......... A61B 2018/00827; A61B 2018/00892; A61B 2018/1206; H02M 3/158; H05H 1/46

See application file for complete search history.

(56) References Cited

U.S. PATENT DOCUMENTS

| | | | |
|---|---|---|---|
| 2014/0035544 A1 | 2/2014 | Chen et al. | |
| 2014/0276750 A1* | 9/2014 | Gilbert | A61B 18/1233 606/33 |
| 2015/0263617 A1 | 9/2015 | Xue | |
| 2016/0336858 A1 | 11/2016 | Nomiyama et al. | |

FOREIGN PATENT DOCUMENTS

| | | |
|---|---|---|
| CN | 101673997 A | 3/2010 |
| CN | 102064677 A | 5/2011 |
| CN | 102111071 A | 9/2011 |
| CN | 103066836 A | 4/2013 |
| CN | 104090614 A | 10/2014 |
| CN | 104980012 A | 10/2015 |
| CN | 105009435 A | 10/2015 |
| CN | 205142007 U | 4/2016 |
| CN | 105915046 A | 8/2016 |
| CN | 205901595 U | 1/2017 |
| EP | 1951005 A1 | 7/2008 |
| EP | 2090249 A1 | 8/2009 |
| EP | 3010131 A1 | 4/2016 |
| JP | 2002010629 A | 1/2002 |
| JP | 2006149056 A | 6/2006 |
| JP | 2009022125 A | 1/2009 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP18808907.2 dated Nov. 16, 2020, 07 pages.

* cited by examiner

ELECTROSURGICAL OUTPUT STAGE WITH INTEGRATED DC REGULATOR

CLAIM OF PRIORITY

This application is a U.S. National Stage Filing under 35 U.S.C. 371 from International Application No. PCT/US2018/035444, filed on May 31, 2018, and published as WO 2018/222903 A1 on Dec. 6, 2018, which claims the benefit of priority to U.S. Provisional Patent Application No. 62/513,287, filed on May 31, 2017, each of which is herein incorporated by reference herein in its entirety.

BACKGROUND

Electrosurgery involves the use of electricity to cause thermal destruction of biological tissue to cut or remove the tissue through desiccation, coagulation, or vaporization, for example. Benefits include the ability to make precise cuts with limited blood loss. Electrosurgical devices are frequently used during surgical procedures to help prevent blood loss in hospital operating rooms or in outpatient procedures. The two types of electrosurgery most commonly used are high-frequency electrosurgery and electrocautery. High-frequency electrosurgery involves high-frequency (radio frequency) alternating current that is converted to heat by resistance as it passes through the tissue. The heat buildup within the tissue causes thermal tissue damage resulting in incision or debulking, for example. Electrocautery also involves direct transference of heat to tissue. Instead of passing electrical current through the tissue, however, the current is used to heat a handheld element, which is then applied to the tissue. Additional modalities of electrosurgery include electrolysis, which uses a chemical reaction created by direct current to damage tissue, and coblation, which uses an electrical current to ionize a conduction medium such as isotonic saline, which is then used to transmit heat to tissue.

A typical electrosurgical generator uses a multi-stage voltage converter to convert alternating current (AC) line power to a controlled radio frequency (RF), output required to perform an electrosurgical procedure. This approach ordinarily includes: first, converting an AC line input to regulated direct current (DC); second, converting the regulated DC to a controlled DC voltage; and third, supplying the controlled DC voltage to an RF output stage. Electrosurgical generators typically include a user interface, that allows the surgeon to adjust the high frequency output voltage, current or power in order to achieve a desired surgical effect.

Prior electrosurgical generator systems typically include a controller to monitor the RF output and adjust the controlled DC voltage to maintain a desired RF output voltage, current and power. During a surgical procedure, an electrosurgical instrument may come in contact with a variety of tissue types and load conditions causing the impedance of the load to vary significantly. Consequently, reasonably tight control generally is required over the controlled DC voltage to adjust the RF output stage voltage to the changing impedances. On a typical system, the controlled DC voltage stage and the RF output stage operate independently, with the controller actively closing a control loop between them.

More specifically, prior switching power supplies often include a first control loop that uses pulse width modulation (PWM) to regulate the converted DC voltage and that include a second control loop under control of a microcontroller to ensure that the controlled DC output responds appropriately to load changes at the RF output stage. The PWM control loop ordinarily operates independent of the RF output stage, and uses its own clock source to generate PWM switching. In essence, prior electrosurgical generator systems often include two control loops running simultaneously to convert an AC line input to an RF output signal. A first PWM control loop in the DC switching regulator ensures that a regulated DC voltage matches a commanded target DC voltage, and a second control loop responsive to the controller adjusts the commanded target DC voltage to adjust the RF output voltage, current and power in response to changes in load at the RF stage.

The use of two control loops can impose limitations upon the responsiveness of a multi-stage voltage converter to fluctuations in RF output loads that have rapidly changing impedance. For example, in some earlier converters, a microcontroller determines a changed target voltage is required in response to a change in RF output load impedance. The changed target voltage is communicated to a DC regulator, which adjusts the controlled DC voltage provided to the RF output stage, which ultimately results in adjustment of the RF output voltage. Since these prior control routines are by nature iterative, the response time to changes in RF load impedance may be limited by the response time of the RF output stage and associated measurement circuitry, along with the response time of the DC regulator circuitry. Since these two sub-systems operate independently, this response time can be significant. A slow response time can lead to situations in which a surgeon detects a noticeable lag in performance which interrupts the surgical flow, or periods in which excessive power is delivered, causing unintended tissue damage.

SUMMARY

A DC-to-DC voltage regulator circuit that includes a pull-up switch and a pull-down switch with an output node between them, A reactive circuit element is coupled to store energy at a voltage level based upon voltage at the output node. A pull-up setting voltage circuit is coupled to provide a pull-up setting voltage as a function of a voltage at the output node. A pull-down setting voltage circuit is coupled to provide a pull-down setting voltage as a function of the voltage at the output node. A first comparator is coupled to cause the pull-up switch to transition between open switch state and its closed switch state based upon a comparison of the pull-up setting voltage and a control voltage. A second comparator is coupled to cause the pull-down switch to transition between its open switch state and its closed switch state.

In another aspect, a method is provided to control switching of a DC-to-DC converter. A pull-up setting voltage is provided that is a function of a voltage at the output node. A pull-down setting voltage is provided that is a function of the voltage at the output node. A first signal is provided to control transition of the pull-up switch between the open switch state and the closed switch state based upon a comparison between the pull-up setting signal and a control signal. A second signal is provided to control transition of the pull-down switch between the open switch state and the closed switch state based upon a comparison between the pull-down setting signal and a control signal.

DESCRIPTION OF EMBODIMENTS

Figure 1:
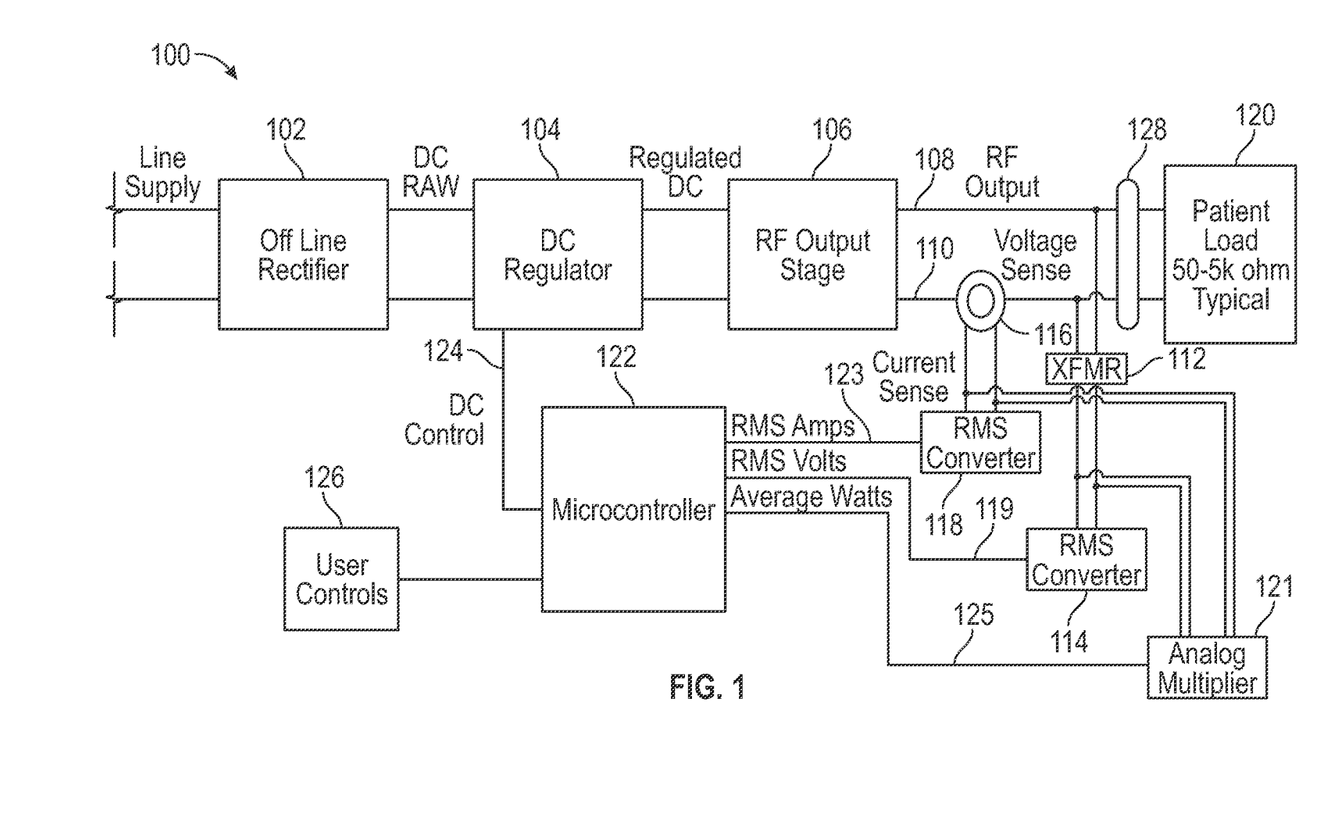
FIG. 1 is an illustrative block diagram representing an electrosurgical generator system.

FIG. 1 is an illustrative block diagram representing an electrosurgical generator system 100 in accordance with some embodiments. The system 100 includes a microcontroller 122, an off line rectifier 102 coupled to convert an AC line voltage signal to a raw rectified DC signal, a DC regulator 104 to convert the rectified DC voltage signal to a controlled DC voltage signal, and an RF output stage 106 coupled to convert the controlled DC voltage to high frequency output energy that can be applied across first and second output terminals 108, 110 at a surgical instrument end effector (not shown). Voltage monitoring circuitry includes a voltage transformer 112 and a first RMS converter 114 coupled to monitor an RF output voltage across the first and second output terminals 108, 110 and to provide an RMS voltage value via line 119 to the microcontroller 122. Current monitoring circuitry includes a current sense transformer 116 and a second RMS converter 118 coupled to monitor an RF output current between the first and second output terminals 108, 110 and to provide via line 123 an RMS current to the microcontroller 122. An analog multiplier circuit 121 is coupled to determine analog RF output power based upon analog RF output voltage and analog RF output current and to provide via line 125 a DC representation of the analog power value to the microcontroller 122. A user input control 126 is coupled to receive user input parameters to the microcontroller 122, which may include a maximum high frequency current, voltage or power, a target high frequency voltage, high frequency current or high frequency power, or some combination of these values, for example.

In operation, the first and second output terminals 108, 110 may be disposed at a surgical instrument end effector 128 to contact two different locations on biological tissue 120. The RF output voltage may represent voltage across the biological tissue 120 between the first and second terminals 108, 110 and the RF output current may represent current passing through the biological tissue 120 between the first and second terminals 108, 110. A microcontroller 122 provides a voltage control signal on control line 124 to the DC regulator 104 to determine the controlled voltage based upon at least one of the RF output voltage and the RF output current and the RF output power and based upon user input received via a user input control block.

More particularly, during a surgical procedure the voltage control signal may be varied based upon variations in impedance measured between the first and second output terminals 108, 110. In general, the impedance load of a patient's biological tissue 120 typically can range from 50 to 5 k ohms, depending on the electrosurgical device used and tissues being targeted. The first RMS converter 114 converts a sensed RF output voltage signal to a first DC feedback signal indicating an RF output voltage level. The second RMS converter 118 converts the sensed RF output current signal to a second DC feedback signal indicating an RF output current level. The analog multiplier circuit 121 converts the sensed RF output voltage and the sensed RF output current to third DC feedback signal indicating average RF output power. The microcontroller 122 produces a voltage control signal on line 124 to cause the DC regulator 104 to produce a controlled DC voltage level that varies based upon at least one of the sensed RF output voltage, the sensed RF output current and the RF output power.

Figure 2:
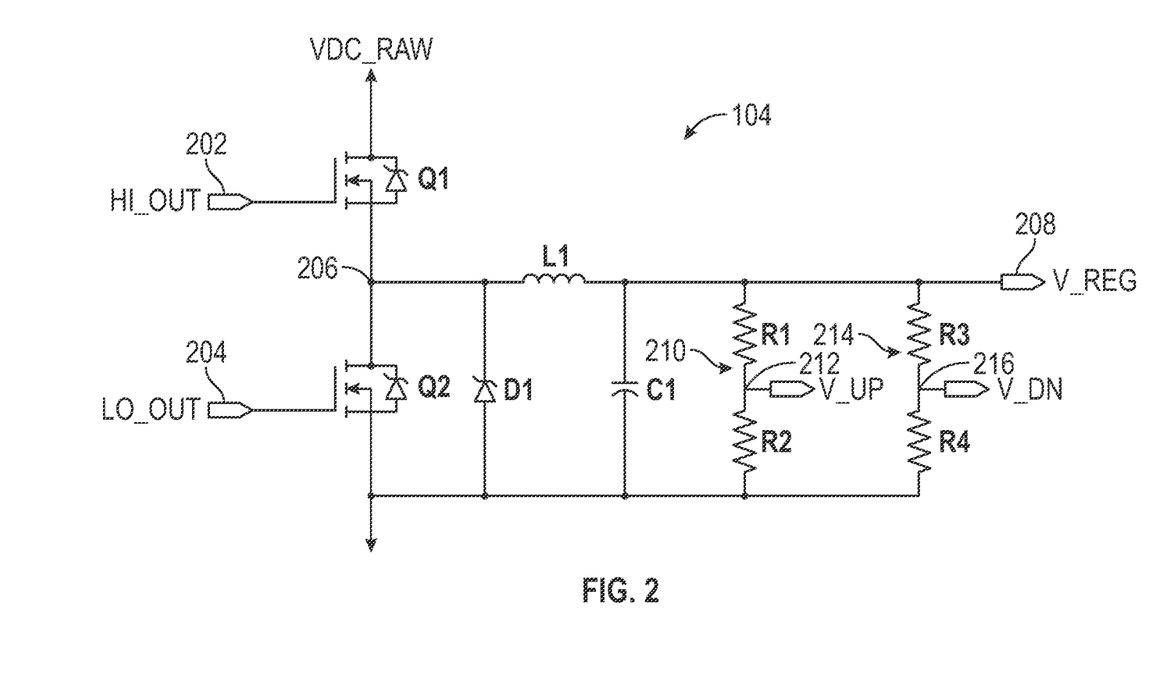
FIG. 2 is an illustrative circuit diagram representing the DC regulator circuit of FIG. 1.

FIG. 2 is an illustrative circuit diagram representing the DC regulator circuit 104 of FIG. 1 in accordance with some embodiments. A pull-up switch Q1 and a pull-down switch Q2 are coupled in series between a pull-up voltage, VDC_RAW, and a pull-down voltage, ground. The pull-up switch Q1 includes a first FET device. The pull-down switch Q2 includes a second FET device. A first gate control node 202 of the first FET device Q1 is coupled to receive a first control signal, HI_OUT. A second gate control node 204 of the second FET device Q2 is coupled to receive a second control signal, LO_OUT. A drain node of the first FET device Q1 is coupled to the pull-up voltage, VDC_RAW. A source node of the first FET device Q1 and a drain node of the second FET device Q2 are coupled to a common node 206. A source node of the second FET device Q2 is coupled to the pull-down voltage, ground. When the DC regulator 104 is in a voltage pull-up state, the pull-up switch Q1 is in a closed state to couple the pull-up voltage to the common node 206, and the pull-down switch Q2 is in an open state to uncouple the common node 206 from the pull-down voltage. When the DC regulator 104 is in a voltage pull-down state, the pull-up switch Q1 is in an open state to uncouple the pull-up voltage from the common node 206, and the pull-down switch Q2 is in a closed state to couple the common node 206 to the pull-down voltage.

Reactive energy storage elements are coupled between the common node and a DC regulator output node. Specifically, a capacitor C1 is coupled in parallel with the second FET device Q2 between a DC regulator output node 208 and ground, and an inductor is coupled in series with the capacitor C1 between the common node 206 and the DC regulator output node 208, A diode D1 is coupled between the common node 206 and the pull-down voltage in parallel with the capacitor C1. More specifically, a cathode of the diode D1 is coupled to the common node 206 between the inductor L1 and the common node 206, and an anode of the diode D1 is coupled to the pull-down voltage.

When the DC regulator 104 is in the pull-up state, the pull-up switch Q1 couples the capacitor C1 to the pull-up voltage to charge the capacitor C1 to the pull-up voltage level, to thereby provide the pull-up voltage at the DC regulator output node 208. Also, while the DC regulator 104 is in the pull-up state, the inductor L1 may regulate a voltage ripple that may be induced by pulsing of the pull-up voltage, which may be inherent in the regulated voltage. When the DC regulator 104 is in the pull-down state, the pull-down switch Q2 couples the capacitor C1 to discharge to thereby provide the pull-down (ground) voltage at the DC regulator output node 208.

During a transition of the DC regulator 104 from the pull-up state to the pull-down state, the inductor L1 damps discharge of the capacitor C1 by preventing it from instantly discharging as the pull-down switch Q2 transitions to the closed state. Also, while the DC regulator 104 transitions from the pull-up state to the pull-down state, the diode D1 damps voltage produced by the inductor L1 by suppressing a spike that may be induced in the inductor L1 when the pull-up switch Q1 is transitioned to its open state. Thus, during a transition of the DC regulator 104 from the pull-up state to the pull-down state, the capacitor C1 and the inductor L1 cooperate to dissipate energy stored in the capacitor C1 in a manner that avoids voltage overshoots and that avoids a sudden discharge of voltage to patient tissue, which could result in unintended tissue damage, as well as excessive smoke generation.

A first divider circuit 210 includes a first resistor R1 and a second resistor R2 that are coupled in series between the DC regulator output node 208, at which a controlled DC regulated voltage, V_REG, is provided, and ground. A first divider node 212 disposed between the first and second resistors R1, R2 provides a pull-up setting voltage, $$V\_UP=R1/(R1+R2)$$

A second divider circuit 214 includes a third resistor R3 and a fourth resistor R4 that are coupled in series between the DC regulator output node 208 and ground. A second divider node 216 disposed between the third and fourth resistors R3, R4 provides a pull-down setting voltage, $$V\_DN=R3/(R3+R4)$$

The resistor values R1 and R2 and the resistor values R3 and R4 are selected such that, $$V\_UP>V\_VDN$$

More specifically, these resistor values are selected so that they do not significantly add to the electrical load of the DC regulator 104 and so that they provide a hysteresis of between 2-10 percent between the pull-up setting voltage and the pull-down setting voltage.

Figure 3:
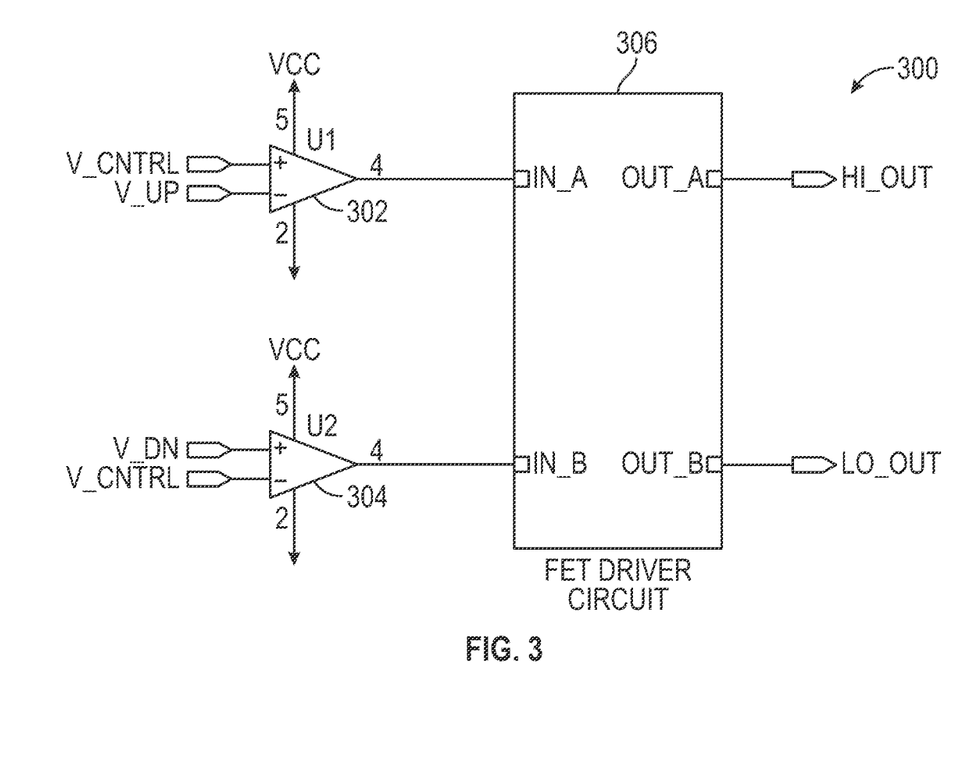
FIG. 3 is an illustrative schematic diagram representing a circuit driver of the system of FIG. 1.

FIG. 3 is an illustrative schematic diagram representing a circuit driver 300 in accordance with some embodiments. A first comparator circuit 302 is coupled to receive a target voltage control signal, V_CNTL, and the pull-up setting voltage, V_UP, and to provide a signal indicative of a value of the first control signal, HI_OUT. More particularly, the first comparator 302 is configured to compare the target voltage control signal, V_CNTL, with the pull-up setting voltage, V_UP, and to provide an output signal indicating turn-on of the pull-up switch Q1 in response to the pull-up setting voltage, V_UP, less than the target voltage control signal. V_CNTL. A second comparator circuit 304 is coupled to receive the target voltage level signal, V_CNTL, aid the pull-down setting voltage, V_DN, and to provide a signal indicative of the second control signal, LO_OUT. More specifically, the second comparator 304 is configured to compare the target voltage control signal, V_CNTL, with the pull-down setting voltage, V_DN, and to provide an output signal indicating turn-on of the pull-down switch Q2 in response to the pull-down setting voltage, V_DN, greater than the target voltage control signal, V_CNTL. A voltage level control circuit 306 is configured to convert logic level outputs of the first and second comparators 302, 304 to voltage levels appropriate for the first and second BET devices Q1, Q2 when used with the regulated voltage, VDC_RAW.

Figure 4:
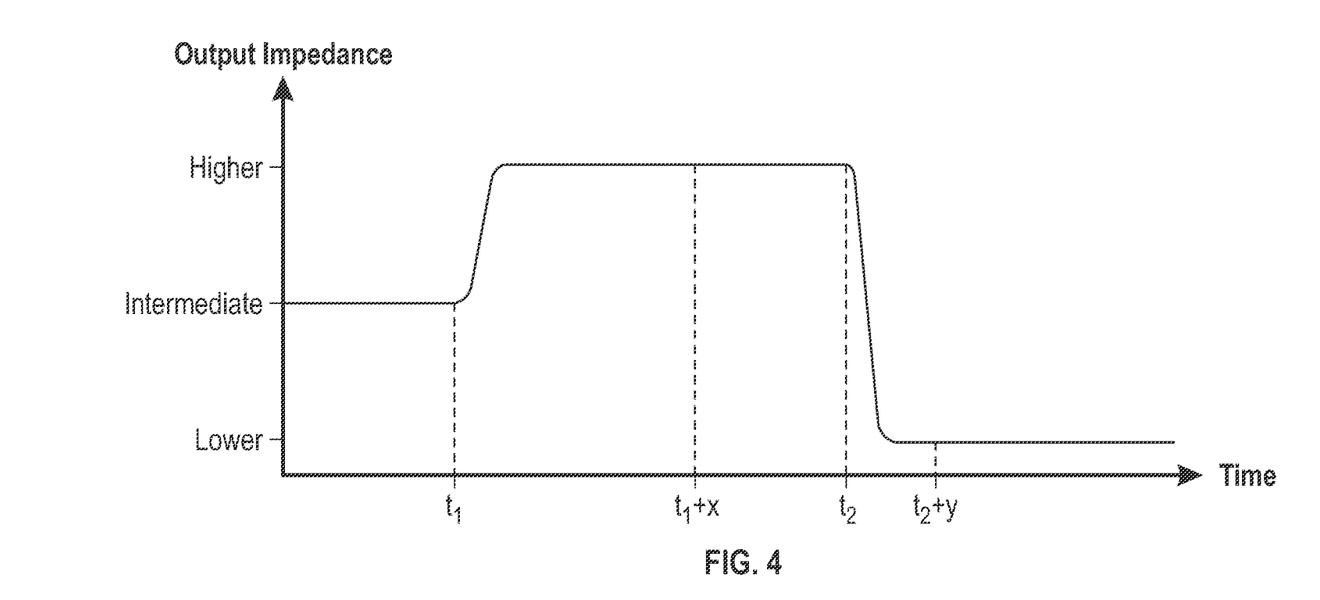
FIG. 4 is an illustrative curve representing example changes in monitored impedance between RF output terminals of the system of FIG. 1.

FIG. 4 is an illustrative curve representing example changes in monitored impedance between the first and second terminals 108, 110 in accordance with some embodiments. During a surgical procedure, the tip of an electrosurgical instrument may move between different tissue portions having different impedances. Typically, the surgical effect of the electrosurgical instrument is directly related to the power delivered to the tissue. Accordingly, RF power is regulated in order to maintain a consistent surgical effect as the instrument is moved by a surgeon between different tissue types. In general, the higher the impedance of the tissue the higher the RB voltage required to provide a desired therapeutic effect at the electrosurgical instrument tip. Conversely, the lower the impedance of the tissue the lower the RF voltage required to provide a desired therapeutic effect at the electrosurgical instrument tip. Providing a voltage that is too high to biological tissue may result in excessive power delivery that may result in excessive tissue heating and unwanted tissue damage. Moreover, during a surgical procedure, an electrosurgical instrument tip may move into and out of contact with patient tissue such as when the tip is momentarily suspended in air above patient tissue, for example. The impedance between the first and second terminals while the tip is suspended in air approaches infinity.

Referring to the example monitored impedance values of FIG. 4, during a time interval $t_0$ to $t_1$, the impedance between the first and second terminals is within a first (intermediate) impedance range of 800-1000 ohms that corresponds to the electrosurgical instrument touching muscular tissue. During a time interval $t_1$ to $t_2$ the impedance between the first and second terminals is within a second (higher) impedance range of 3000-4000 ohms that corresponds to the electrosurgical instrument touching fatty tissue. During a time interval $t_2$ to $t_3$, the impedance between the first and second is within a third (lower) impedance range of 200-500 ohms that corresponds to the electrosurgical instrument touching bleeding, well vascularized tissue.

Figure 5A:
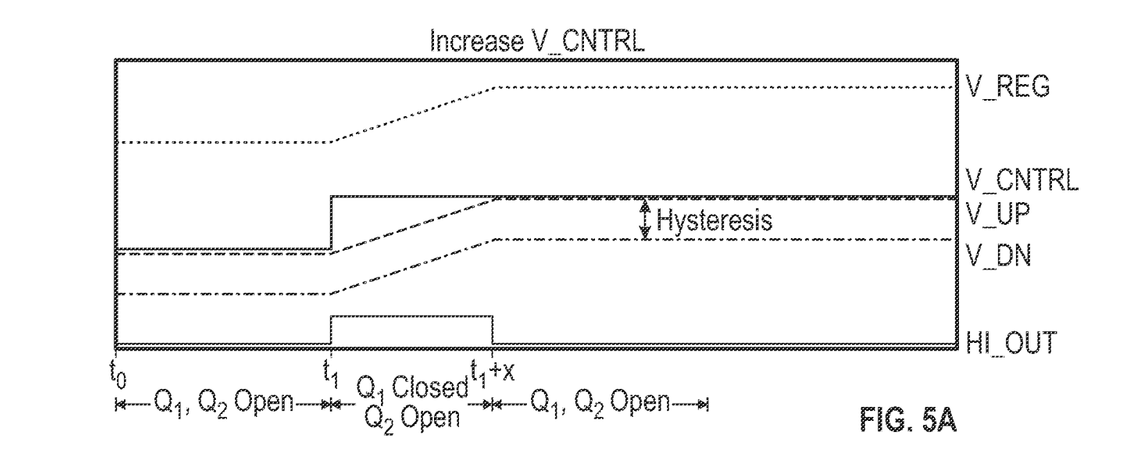
FIGS. 5A-5B are illustrative signal timing diagrams representing operation of the DC regulator in response to the illustrative example variations in impedance of FIG. 4.
Figure 5B:
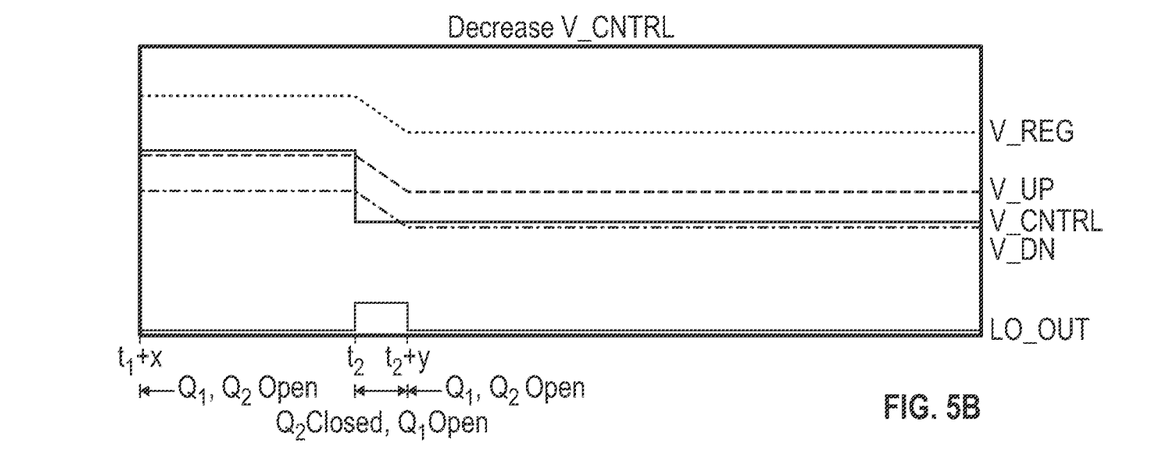

FIGS. 5A-5B are illustrative signal timing diagrams representing operation of the DC regulator 104 in response to the illustrative example variations in impedance of FIG. 4. FIG. 5A illustrates changes in the first control signal, HI_OUT, and the regulated DC voltage, V_REG, in response to changes in the voltage control signal, V_CNTL and the pull-up setting voltage, V_UP. FIG. 5B illustrates changes in the second control signal, LO_OUT and the regulated DC voltage, V_REG, in response to changes in the voltage control signal, V_CNTL, and the pull-down setting voltage, V_DN.

Referring to FIG. 4 and FIG. 5A, during time interval $t_0$ to $t_1$, while the monitored impedance across first and second output terminals 108, 110 is in the illustrative example first (intermediate) impedance range, the first control signal, HI_OUT, has a value to open the pull-up switch Q1 to decouple the common node 206 from the pull-up voltage, VDC_RAW. It is noted that during time interval $t_0$ to $t_1$ the second control signal, LO_OUT (not shown) has a value to also open the pull-down switch Q2 to decouple the common node 206 from the ground voltage level. As shown in FIG. 4, at time $t_1$, the monitored impedance changes to the second (higher) impedance range. In response to the increased impedance, the microcontroller 122 produces a digital step increase in the voltage control signal, V_CNTRL. In response to the step increase in the voltage control signal, V_CNTRL, the circuit driver 300 produces a digital step increase in the first control signal, HI_OUT, which causes the pull-up switch Q1 to close to couple the common node 206 to the pull-up voltage, VDC_RAW, which causes charge to flow to the capacitor C1, which results in a corresponding build up in the DC regulated voltage V_REG at the output node 208 and in the pull-up setting voltage. V_UP, and the pull-down setting voltage, V_DN. More specifically, the DC regulated voltage, V_REG, pull-up setting voltage, V_UP, and pull-down setting voltage. V_DN, increase with the charge build-up on the capacitor C1. At time $t_{1+x}$, in response to the pull-up setting voltage, V_UP, reaching a voltage level that substantially matches the voltage control signal, V_CNTRL, the circuit driver 300 produces a digital step decrease in the first control signal, HI_OUT, which causes the pull-up switch Q1 to open to decouple the common node 206 from the pull-up voltage, VDC_RAW. It is noted that the pull-down switch Q2 remains open and the common node 206 remains decoupled from ground. Thus, in response to the increase in impedance at time $t_1$, the voltage microcontroller 122 produces a step increase in the V_CNTL signal, which causes increases in the voltage values of V_REG, V_UP and V_DN. The increased value of V_REG acts to maintain a steady RF power across the first and second output terminals 108, 110 despite the increased impedance between them. The increased value of V_UP acts to cause the circuit driver 300 to open the pull-up switch Q1 in response to the pull-up voltage V_UP rising to a level indicated by the stepped-up V_CNTL voltage, Referring to FIG. 4 and FIG. 5B, a during time interval $t_{1+x}$ to $t_2$, while the monitored impedance across first and second output terminals 108, 110 is in the illustrative example second (high) impedance range, the second control signal, LO_OUT, has a value to open the pull-down switch Q2 to decouple the common node 206 from the pull-down voltage, ground. It is noted that during time interval $t_{1+x}$ to $t_2$ the first control signal, HI_OUT (not shown) has a value to also open the pull-up switch Q1 to decouple the common node 206 from the pull-up voltage, VDC_RAW. As shown in FIG. 4, at time $t_2$, the monitored impedance changes to the third (lower) impedance range. In response to the reduced impedance, the microcontroller 122 produces a digital step decrease in the voltage control signal, V_CNTRL. In response to the step decrease in the voltage control signal, V_CNTRL, the circuit driver 300 produces a digital step increase in the second control signal, LO_OUT, which causes the pull-down switch Q2 to close to couple the common node 206 to the pull-down voltage, ground, which causes a discharge of charge from the capacitor C1, which results in a corresponding decrease in the DC regulated voltage V_REG at the output node 208 and in the pull-up setting voltage, V_UP, and the pull-down setting voltage, V_DN. More specifically, the DC regulated voltage, V_REG, pull-down setting voltage, V_DN, and pull-up setting voltage, V_UP, decrease with the discharge of charge from the capacitor C1. At time $t_{2+y}$, in response to the pull-down setting voltage, V_DN, reaching a voltage level that substantially matches the voltage control signal, V_CNTRL, the circuit driver 300 produces a digital step decrease in the second control signal, LO_OUT, which causes the pull-down switch Q2 to open to decouple the common node 206 from the pull-down voltage, ground. It is noted that the pull-ups switch Q1 remains open and the common node 206 remains decoupled from the pull-up voltage, VDC_RAW, Thus, in response to the decrease in impedance at time $t_2$, the voltage microcontroller 122 produces a step decrease in the V_CNTL signal, which causes decreases in the voltage values of V_REG, V_DN and V_UP. The decreased value of V_REG acts to maintain a steady RF power across the first and second output terminals 108, 110 despite the decreased impedance between them. The decreased value of V_DN acts to cause the circuit driver 300 to open the pull-down switch Q2 in response to the pull-down voltage V_DN decreasing to a level indicated by the stepped-down V_CNTL voltage.

Figure 6:
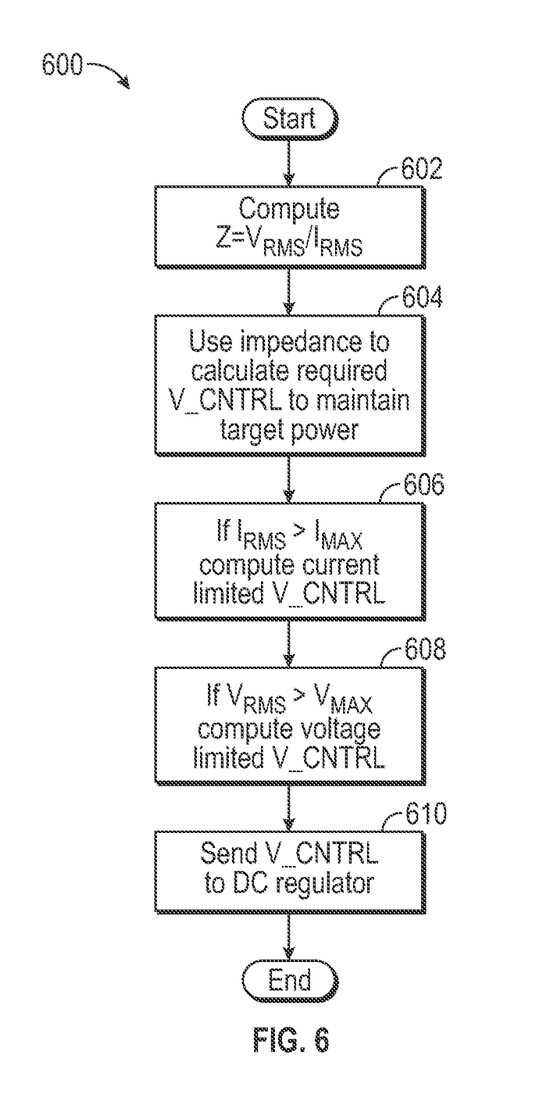
FIG. 6 is an illustrative flow diagram representing configuration of a microcontroller of the system of FIG. 1 to produce changes in a voltage control signal in response to changes in impedance between the RF output terminals.

FIG. 6 is an illustrative flow diagram 600 representing configuration of the microcontroller 122 to produce the voltage control signal, V_CNTL, in response to impedance between RF output terminals 108, 110. Block 602 determines impedance based upon measured $V_{RMS}$ and $I_{RMS}$ in accordance with the formulation.

$$Z = V_{RMS}/I_{RMS}$$

Block 604 uses the determined impedance as a basis to determine a value of the voltage control signal, V_CNTL, to cause the DC regulator 104 to vary the regulated voltage, V_REG, to cause a steady target RF power level despite variations in impedance across the output terminals 108, 110.

A determination of a value for the voltage control signal may be based upon the well-known relationship, $$P = V^2/Z$$

In some embodiments, a value for the voltage control signal may be based upon an algorithm such as a Proportional-Integral-Derivative control loop. A target RF power level may be user-specified or dependent upon a surgical procedure, for example.

Block 606 may adjust the voltage control signal, V_CNTL, based upon a comparison of a present monitored $I_{RMS}$ current and threshold maximum LAX current. An $I_{MAX}$ current may be user-specified or dependent upon a surgical procedure, for example. Block 608 may adjust the voltage control signal, V_CNTL, based upon a comparison of a present monitored $V_{RMS}$ voltage and threshold maximum $V_{MAX}$ current. A $V_{MAX}$ voltage may be user-specified or dependent upon a surgical procedure, for example. Block 610 transmits the determined variable voltage control signal, V_CNTL, to the circuit driver 300 for use in control of the DC regulator 104.

The above description is presented to enable any person skilled in the art to create and use an electrosurgical output stage with integrated regulator. Various modifications to the embodiments will be clear to those skilled in the art, and the generic principles defined herein may be applied to other embodiments and applications without departing from the spirit and scope of the invention. In the preceding description, numerous details are set forth for explanation. However, one of ordinary skill in the art will realize that the circuitry might be practiced without the use of these specific details. In other instances, well-known circuits and processes are shown in block diagram form in order not to obscure the description of the invention with unnecessary detail. Identical reference numerals may be used to represent different views of the same or similar item in different drawings and in the specification. Thus, the foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims.

The invention claimed is:

1. A DC-to-DC voltage regulator circuit comprising:
   an output node;
   a pull-up switch having a closed switch state to couple a DC pull-up voltage to the output node and having an open switch state to uncouple the DC pull-up voltage from the output node;
   a pull-down switch having a closed switch state to couple the output node to a ground voltage and having an open switch state to uncouple the output node from the ground voltage;
   a reactive circuit element coupled to store energy at a voltage level based upon voltage at the output node;

a pull-up setting voltage divider circuit coupled to provide a pull-up setting voltage at a pull-up setting divider node that is a function of a voltage at the output node;
a pull-down setting voltage divider circuit coupled to provide a pull-down setting voltage at a pull-down setting divider node that is a function of the voltage at the output node;
a control circuit to produce a control voltage having a value that is a function of an impedance at an end effector of a surgical instrument;
a first comparator coupled to cause the pull-up switch to transition between open switch state and its closed switch state based upon a comparison of the pull-up setting voltage and the control voltage; and
a second comparator coupled to cause the pull-down switch to transition between its open switch state and its closed switch state based upon a comparison of the pull-down setting voltage and the control voltage.

2. The DC-to-DC voltage regulator circuit of claim 1,
wherein the pull-down switch includes a first transistor; and
wherein the pull-down switch includes a second transistor.

3. The DC-to-DC voltage regulator circuit of claim 1,
wherein the first comparator coupled to cause the pull-up switch to transition to its closed switch state in response to the pull-up setting voltage having a magnitude less than the control voltage and to transition to its open switch state in response to the pull-up setting voltage having a magnitude greater than the control voltage; and
wherein the second comparator coupled to cause the pull-down switch to transition to its closed switch state in response to the pull-down setting voltage having a magnitude greater than the control voltage and to transition to its open switch state in response to the pull-down setting voltage having a magnitude less than the control voltage.

4. The DC-to-DC voltage regulator circuit of claim 3,
wherein the pull-up setting voltage is greater than the pull-down setting voltage.

5. The DC-to-DC voltage regulator circuit of claim 1,
wherein the reactive circuit element includes a capacitor.

6. The DC-to-DC voltage regulator circuit of claim 1,
wherein the reactive circuit element includes a capacitor and an inductor.

7. The DC-to-DC voltage regulator circuit of claim 6,
wherein the capacitor and the inductor are arranged to damp discharge of the capacitor in response to closing of the pull-down switch.

8. The DC-to-DC voltage regulator circuit of claim 1,
wherein the reactive circuit element includes a capacitor; further including:
an inductor coupled to prevent instantaneous discharge of the capacitor in response to a transition of the pull-down switch to a closed switch state.

9. The DC-to-DC voltage regulator circuit of claim 1,
wherein the reactive circuit element includes a capacitor; further including:
an inductor coupled to prevent instantaneous discharge of the capacitor in response to a transition of the pull-down switch to a closed switch state; and
a diode coupled to suppress a spike induced in the inductor when the pull-up switch transitions to an open state.

10. The DC-to-DC voltage regulator circuit of claim 1 further including:

the control circuit to produce the control voltage having a value that is a function of a user selected control parameter.

11. The DC-to-DC voltage regulator circuit of claim 1 further including:
the control circuit to produce the control voltage, wherein the control voltage having a value that increases with an increase in the impedance at an end effector of a surgical instrument.

12. The DC-to-DC voltage regulator circuit of claim 1 further including:
the control circuit to produce the control voltage, wherein the control voltage having a value that decreases with a decrease in the impedance at an end effector of a surgical instrument; and
the control circuit to produce the control voltage having a value that increases with an increase in the impedance at an end effector of a surgical instrument.

13. The DC-to-DC voltage regulator circuit of claim 1 further including:
the control circuit to produce the control voltage, wherein the control voltage having a value between the pull-up setting voltage and the pull-down setting voltage when an impedance at an end effector matches a selected target impedance.

14. The DC-to-DC voltage regulator circuit of claim 1,
wherein the pull-up setting voltage divider circuit including at least two resistors coupled to provide a pull-up setting voltage at a pull-up setting divider node that is a function of a voltage at the output node;
wherein the pull-down setting voltage divider circuit including at least two resistors coupled to provide a pull-down setting voltage at a pull-down setting divider node that is a function of the voltage at the output node; and
wherein the at least two resistors of the pull-up setting voltage divider circuit and the at least two resistors of the pull-down setting voltage divider circuit having resistor values selected to provide a hysteresis between the pull-up setting voltage and the pull-down setting voltage.

15. The DC-to-DC voltage regulator circuit of claim 14:
wherein the hysteresis between the pull-up setting voltage and the pull-down setting voltage is in a range of between 2-10 percent.

16. ADC-to-DC voltage regulator circuit comprising:
an output node;
a pull-up switch having a closed switch state to couple a DC pull-up voltage to the output node and having an open switch state to uncouple the DC pull-up voltage from the output node;
a pull-down switch having a closed switch state to couple the output node to a ground voltage and having an open switch state to uncouple the output node from the ground voltage;
a capacitor coupled to store energy at a voltage level based upon voltage at the output node;
a pull-up setting voltage divider circuit coupled to provide a pull-up setting voltage at a pull-up setting divider node that is a function of a voltage at the output node;
a pull-down setting voltage divider circuit coupled to provide a pull-down setting voltage at a pull-down setting divider node that is a function of the voltage at the output node, wherein the pull-up setting voltage is greater than the pull-down setting voltage;
a voltage discharge damping circuit coupled damp a voltage discharge of the capacitor;

a control circuit to produce a control voltage having a value that is a function of an impedance at an end effector of a surgical instrument;

a first comparator coupled to cause the pull-up switch to transition to its closed switch state in response to the pull-up setting voltage having a magnitude less than the control voltage and to transition to its open switch state in response to the pull-up setting voltage having a magnitude greater than the control voltage; and a second comparator coupled to cause the pull-down switch to transition to its closed switch state in response to the pull-down setting voltage having a magnitude greater than the control voltage and to transition to its open switch state in response to the pull-down setting voltage having a magnitude less than the control voltage.

17. The DC-to-DC voltage regulator circuit of claim 16, wherein the pull-up setting voltage divider circuit including at least two resistors coupled to provide a pull-up setting voltage at a pull-up setting divider node that is a function of a voltage at the output node;

wherein the pull-down setting voltage divider circuit including at least two resistors coupled to provide a pull-down setting voltage at a pull-down setting divider node that is a function of the voltage at the output node; and wherein the at least two resistors of the pull-up setting voltage divider circuit and the at least two resistors of the pull-down setting voltage divider circuit having resistor values selected to provide a hysteresis between the pull-up setting voltage and the pull-down setting voltage.

18. The DC-to-DC voltage regulator circuit of claim 17:

wherein the hysteresis between the pull-up setting voltage and the pull-down setting voltage is in a range of between 2-10 percent.

19. A method to control switching of a DC-to-DC converter that includes output node; a pull-up switch having a closed switch state to couple a DC pull-up voltage to the output node and having an open switch state to uncouple the DC pull-up voltage from the output node; a pull-down switch having a closed switch state to couple the output node to a ground voltage and having an open switch state to uncouple the output node from the ground voltage; a reactive circuit element coupled to store energy at a voltage level based upon voltage at the output node, the method comprising:

providing a pull-up setting voltage that is a function of a voltage at the output node;

providing a pull-down setting voltage that is a function of the voltage at the output node;

producing a voltage control signal as a function of an impedance at an end effector of a surgical instrument;

producing a first signal to control transition of the pull-up switch between the open switch state and the closed switch state based upon a comparison between the pull-up setting signal and the voltage control signal; and producing a second signal to control transition of the pull-down switch between the open switch state and the closed switch state based upon a comparison between the pull-down setting signal and the voltage control signal.

20. The method of claim 19, wherein the pull-up setting voltage is greater than the pull-down setting voltage.

21. The method of claim 19 further including:

damping a discharge from the reactive circuit element in response to a transition of the pull-down switch to a closed state.

22. The method of claim 19, wherein producing the first signal includes producing the first signal having a value to close the pull-up switch in response to the first signal having a value less than a value of the voltage control signal; and wherein producing the second signal includes producing the second signal having a value to close the pull-down switch in response to the second signal having a value greater than a value of the voltage control signal.

23. The method of claim 19, further including:

using at least two resistors of a pull-up setting voltage divider circuit and at least two resistors of a pull-down setting voltage divider circuit to provide a hysteresis between the pull-up setting voltage and the pull-down setting voltage.

24. The method of claim 23:

wherein the hysteresis between the pull-up setting voltage and the pull-down setting voltage is in a range of between 2-10 percent.

* * * * *

UNITED STATES PATENT AND TRADEMARK OFFICE
CERTIFICATE OF CORRECTION

PATENT NO. : 11,701,163 B2
APPLICATION NO. : 16/616717
DATED : July 18, 2023
INVENTOR(S) : Duane W. Marion Page 1 of 1

It is certified that error appears in the above-identified patent and that said Letters Patent is hereby corrected as shown below:

In the Claims

Column 10, Claim 16, Line 46, please delete "ADC-to-DC" and insert --A DC-to-DC--.

Signed and Sealed this
Fifth Day of September, 2023

Katherine Kelly Vidal
*Director of the United States Patent and Trademark Office*